United States Patent
Lippincott, III et al.

[11] Patent Number: 6,059,830
[45] Date of Patent: *May 9, 2000

[54] LOW WEAR BALL AND CUP JOINT PROSTHESIS

[75] Inventors: Albert L. Lippincott, III, Prior Lake, Minn.; John B. Medley, Fergus, Canada

[73] Assignee: Wright Medical Technology, Inc., Arlington, Tenn.

[*] Notice: This patent issued on a continued prosecution application filed under 37 CFR 1.53(d), and is subject to the twenty year patent term provisions of 35 U.S.C. 154(a)(2).

[21] Appl. No.: 09/066,389
[22] PCT Filed: Nov. 1, 1996
[86] PCT No.: PCT/US96/17371
§ 371 Date: Aug. 3, 1998
§ 102(e) Date: Aug. 3, 1998
[87] PCT Pub. No.: WO97/16138
PCT Pub. Date: May 9, 1997

Related U.S. Application Data
[60] Provisional application No. 60/006,172, Nov. 2, 1995.
[51] Int. Cl.[7] .................................................. A61F 2/30
[52] U.S. Cl. .................................. 623/18; 623/23; 623/22
[58] Field of Search .................................. 623/18, 22, 23

[56] References Cited

U.S. PATENT DOCUMENTS

| | | |
|---|---|---|
| 3,510,883 | 5/1970 | Cathcart, III . |
| 3,521,302 | 7/1970 | Muller .................................... 623/22 X |
| 4,031,570 | 6/1977 | Frey . |
| 4,784,662 | 11/1988 | Muller ...................................... 623/22 |
| 4,840,632 | 6/1989 | Kampner .................................. 623/22 |
| 5,609,643 | 3/1997 | Colleran et al. .......................... 623/20 |
| 5,641,323 | 6/1997 | Caldarise ................................. 623/22 |

FOREIGN PATENT DOCUMENTS

| | | |
|---|---|---|
| 302850 | 2/1989 | European Pat. Off. . |
| 648478 | 4/1995 | European Pat. Off. . |
| 681815 | 11/1995 | European Pat. Off. . |
| 2134170 | 12/1972 | France . |
| 95/23566 | 9/1995 | WIPO . |

*Primary Examiner*—Jeffrey A. Smith
*Attorney, Agent, or Firm*—Fredrikson & Byron, PA

[57] ABSTRACT

A ball (14) and cup (18) prosthesis is provided with articulating metal surfaces (25, 24), the surfaces (25, 24) having an area of intimate contact (θ) in which the surfaces (25, 24) are formed on radii ($R_3$, $R_1$) which differ by at most 50 micrometers. The area of intimate contact (θ) has a surface area that ranges from 0.12 $\pi R_3^2$ to 1.65 $\pi R_3^2$, and the centerline average surface roughness of the metal articulating surfaces (25, 24) in the area of intimate contact (θ) preferably is not greater than 0.1 micrometers.

20 Claims, 3 Drawing Sheets

LOW WEAR BALL AND CUP JOINT PROSTHESIS

CROSS-REFERENCE TO RELATED APPLICATIONS

This application claims the benefit under 35 U.S.C. §119 (e) of U.S. provisional application 60/006,172 filed Nov. 2, 1995.

FIELD OF THE INVENTION

The invention relates to implantable joint prostheses particularly adapted for the replacement of diseased or injured ball and cup joints.

BACKGROUND OF THE INVENTION

Implantable ball and cup (socket) joints that are commercially available commonly consist of an implantable cup or socket that provides a generally hemispherical surface and that is made from a plastic such as ultra high molecular weight polyethylene, and a ball member that is made from a metal such as cobalt-chrome alloys. Usage of the implanted joint can result in significant wearing of the plastic cup portion, and this can in turn lead to such problems as wear particle-induced osteolysis which involves the development of large, soft tissue cysts where bone once existed. As a result of osteolysis, the bony support for both the cup and ball elements of a prosthesis may be weakened significantly, leading to loosening of these elements.

To reduce the amount of debris formed by wearing of a plastic surface, it would be desirable to make both the ball and cup articulating surfaces of a hard, wear-resistant substance such as a ceramic or a metal such as a cobalt-chrome alloy. The basic concept of utilizing metal-to-metal articulating surfaces for a prosthetic device is not new; reference is made to Walker, P. S., and B. L. Gold, *The Tribology (Friction, Lubrication and Wear) of All-Metal Artificial Hip Joints, Wear* 17:285–299, 1971, and to Notton, U.S. Pat. No. 4,263,681; Hintermann, U.S. Pat. No. 4,687,487; Sivash, U.S. Pat. No. 3,943,576; and Shersher, U.S. Pat. No. 3,859,669. The geometry of ball and cup prostheses also are discussed in Frey, U.S. Pat. No. 4,031,570; Müller, U.S. Pat. No. 4,784,662; and Fisher, PCT Publication No. WO 95/23566.

When the articulating surfaces of ball and cup joints are made of metal, however, wear continues to be a problem, it appears. There is an initial high rate of wear during the "wear in" period in which the ball or the cup or both are worn down to the point where they develop surfaces that fit with some snugness against one another, and as this occurs, the rate of wear gradually decreases. The small particles resulting particularly during the initial period of high wear are liberated into the synovial fluid that lubricates joint cavities and can be distributed into surrounding tissues; there is concern that this can lead to medical problems of the type encountered when polymeric surfaces are employed, as described above.

When the articulating surfaces of an all-metal ball and cup joint have worn down to the point where the wear rate has been reduced, commonly the wearing away process is found to have formed one or more ridges on the articulating surface of either the ball or the cup or both, the ridges delimiting the snug area or areas of contact between these surfaces. The ridges, while not interfering with normal articulating movement of the joint, none-the-less may accelerate wear during large range-of-motion movements and/or interfere with the entrainment of lubricating synovial fluid.

SUMMARY OF THE INVENTION

By carefully sculpting the articulating hard surfaces of ball and cup joints, the "wearing in" normally associated with such joints can be largely avoided, as can the formation of ridges on the ball or cup articulating surfaces.

In its broader aspect, the invention relates to an articulating ball and cup joint prosthesis for use between two normally articulating bones. The prosthesis comprises an articulating cup attachable to one of the bones and comprising a body having a generally hemispheric cavity provided with a first hard spheroidal articulating surface formed on a radius $R_1$. A second articulating member is provided having a generally ball-shaped body attachable to the other of the bones and having a second spheroidal hard articulating surface slidingly contacting the first articulating surface in an area of intimate contact, the second articulating surface being formed on a radius $R_3$.

"Area of intimate contact," as used herein, means that area in which the surfaces defined by the radii $R_1$ and $R_3$ are in contact where $R_1$ differs from $R_3$ by no more than 50 micrometers, desirably by no more than 25 micrometers, preferably by no more that 6 micrometers and most preferably by no more than 2 micrometers. The respective spheroidal surfaces of the first and second members are formed so that the area of intimate contact ranges from $0.12\,\pi R_3^2$ to $1.65\,\pi R_3^2$, and preferably from $0.2\,\pi R_3^2$ to $0.7\,\pi R_3^2$. Expressed in different terms, the area of intimate contact is the area of the spherical segment subtended by the solid angle $\phi$ formed on radius $R_3$ where $\phi$ ranges from 40 degrees to 160 degrees and preferably from 50 degrees to 100 degrees.

The respective spheroidal surfaces also provide a closely spaced but non contact area between them as they diverge immediately adjacent the area of intimate contact, the surfaces in the non contact area being characterized by the relationship $h = s^2/2R \pm 20\%$ in which "h" is the gap between the diverging surfaces of the ball and cup at a distance "s" from the edge of the area of intimate contact measured along the arc swept out by the radius $R_1$, and $R = (R_4 R_2)/(R_4 - R_2)$ where $R_4$ and $R_2$ are the respective radii of the cup and the ball immediately adjacent the area of intimate contact. Expressed in different terms, for a location spaced from the area of intimate contact by the angle $\theta$ swept out by the radius $R_3$ away from the apex of the cup, the gap h is within 20% of the value of the expression $(R_1\theta)^2/2R$ in which R is as defined above and $\theta$ is expressed in radians. When $\theta$ is less than about 0.5 radians, the expression $(R_1\theta)^2/2R$ defines the gap h within plus or minus 3%.

DETAILED DESCRIPTION OF THE PREFERRED EMBODIMENT

"Intimate contact area" means the sliding area of the hard articulating surfaces of the cup and ball in which $R_1$ differs from $R_3$ by no more than 50 micrometers, desirably by no more that 25 micrometers, preferably by no more than six micrometers, and most preferably by no more than two micrometers. On a microscopic level, any metal, ceramic, or other hard surface is somewhat rough and jagged, the surface having peaks and valleys. Reference is made to Mummery, L., *Surface Texture Analysis The Handbook*, Hommelwerke GmbH, 1992, which is incorporated herein by reference. Preferably, the centerline average surface roughness of the articulating surfaces in the area of intimate contact is not greater than 0.1 micrometers and preferably not greater than 0.025 micrometers.

Figure 2:
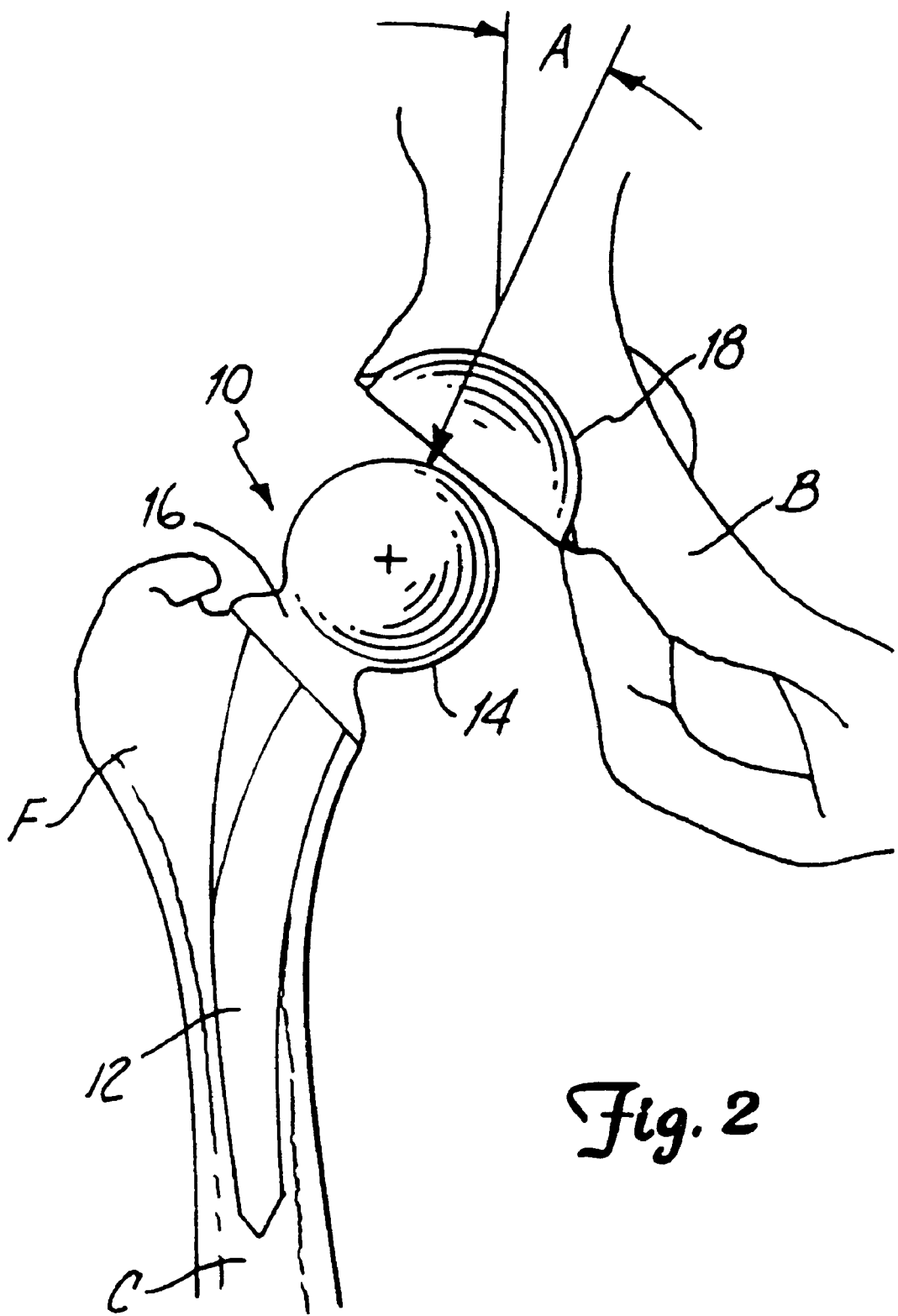
FIG. 2 is a perspective broken-away view of a hip prosthesis embodying a ball and cup joint prosthesis of the invention.

Referring first to FIG. 2, the proximal portion of the human femur is shown at "F", and the adjacent acetabulum of the pelvis is shown as "B". As shown, a femoral prosthesis 10 is implanted in the proximal end of the intermedullary canal of the femur by well known surgical procedures, the femoral prosthesis comprising a stem 12 that is received in the intermedullary canal and an articulating ball 14 joined to the stem 12 by a connector such as the connecting neck 16, the neck positioning the ball at an angle to the axis of the femur to enable it to articulate in the cup. Shown at 18 in FIGS. 2 and 3 is an acetabular cup prosthesis which is implanted in the acetabulum by any of a number of similarly well known surgical procedures.

The surgical procedures employed in anchoring a femoral prosthesis and an acetabular cup prosthesis in the proximal end of the femur and in the acetabulum, respectively, have been widely reported. Commonly, the bony acetabulum is exposed and is surgically sculpted to receive a cup prosthesis such as that shown at 18 in FIG. 3. The cup prosthesis may be provided with an outer convex surface 20 that is appropriately roughened or otherwise treated so as to promote good adhesion to bone cement or to promote ingrowth of bony tissue in the event that cement is not employed. Screws or other attachments may be employed to more securely anchor the cup to the acetabulum. In FIG. 3, fins 22 are positioned on the outer rim of the cup and become embedded in the hard bony rim of the acetabulum as the cup is forced into place. As mentioned above, bone cement commonly is employed to anchor the cup to the bony acetabulum.

Figure 3:
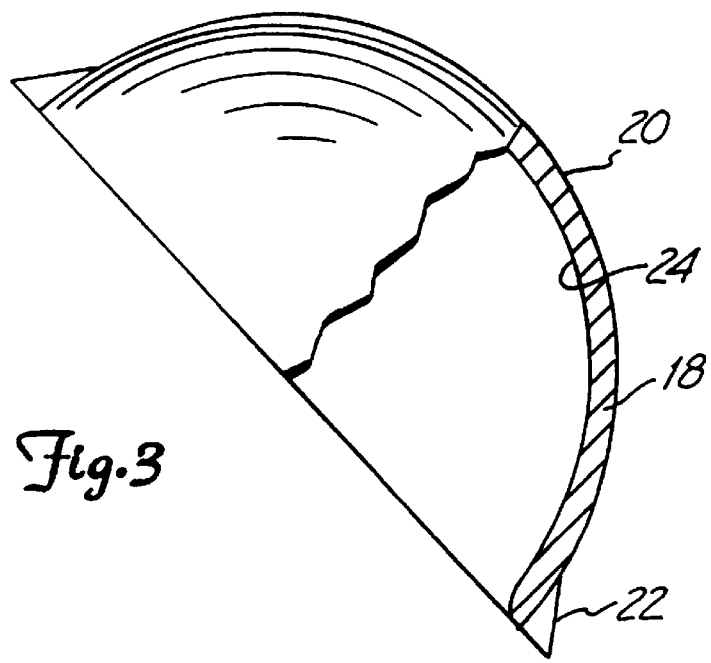
FIG. 3 is a side view, in partial cross-section, of the cup portion of a prosthesis of the invention.

The cup shown in FIG. 3 is depicted as being of metal and having a metallic inner articulating surface 24. However, the cup may consist of several elements. For example, an outer shell similar to that shown in FIG. 3 may be provided for attachment to the bony acetabulum, and an inner generally hemispheric shell may be carried by the outer shell, the inner shell having a concave, generally spheroidal hard articulating surface.

Referring to the femoral prosthesis 10 of FIG. 2, the intermedullary canal "C" of the femur commonly is surgically prepared to receive the stem 12 of the prosthesis, and the stem may be either cemented in place using typical bone cement or may be provided with an exterior surface which is tightly received in the intermedullary canal and which promotes and supports bone growth. The ball 14 is attached by means of the neck 16 to the stem and is provided with a hard outer surface 25 (FIG. 1) which is carefully formed and configured to articulate with the interior hard articulating surface 24 of the cup. The invention relates to the nature of the articulating interaction between the spheroidal articulating hard surfaces of the ball and cup, and it is to this interaction that we now turn.

Figure 1:
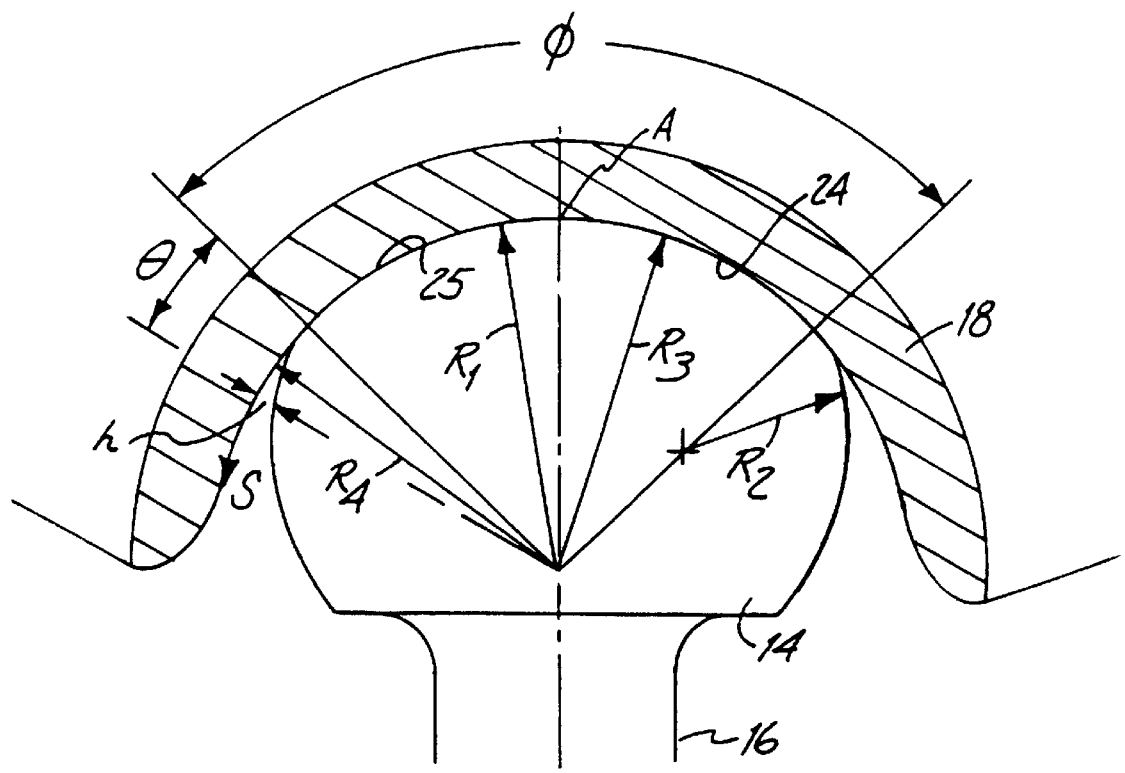
FIG. 1 is a broken-away schematic view in partial cross section of the articulating surfaces of a ball and cup joint prosthesis of the invention with the cup member shown in cross-section.
Figure 4:
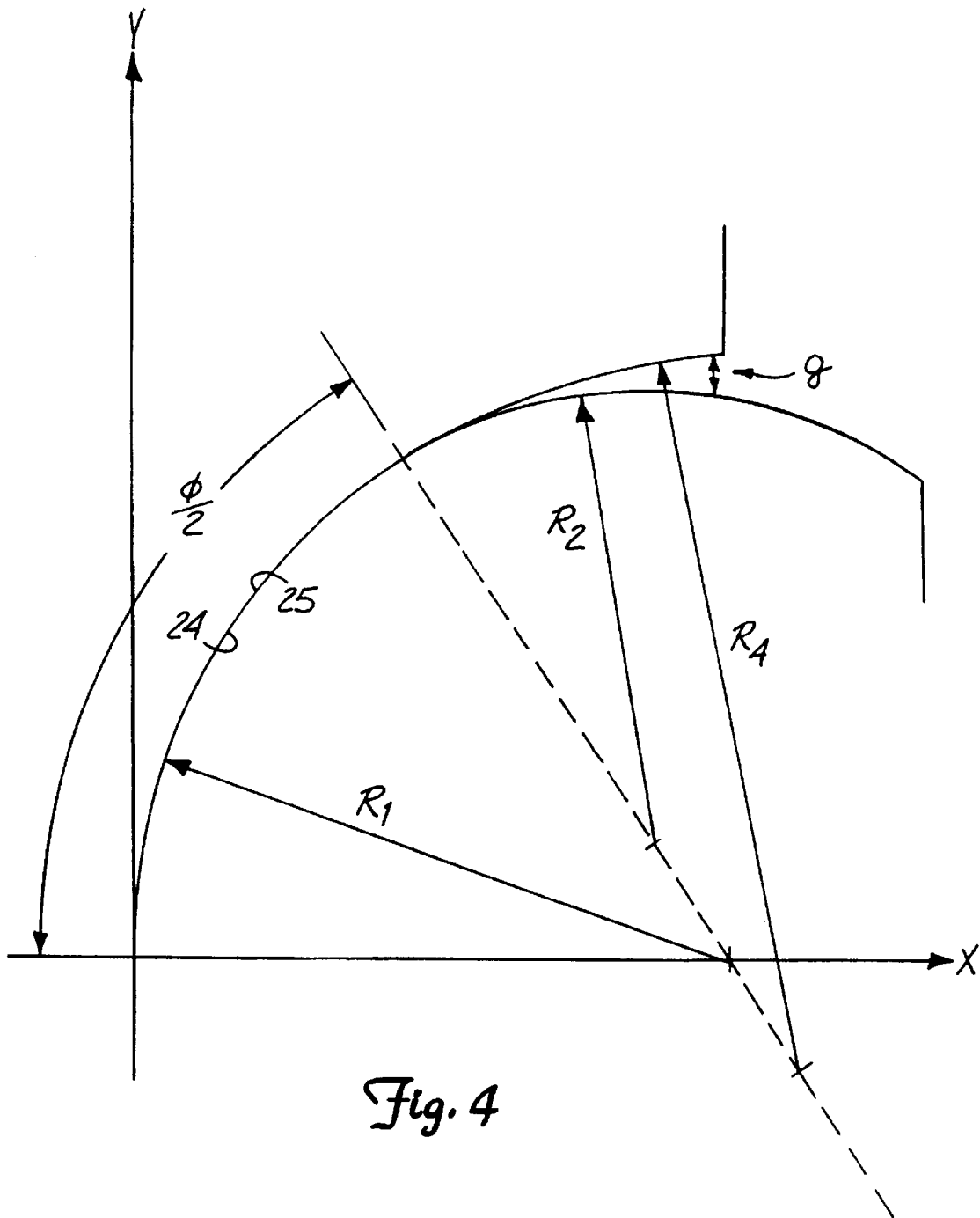
FIG. 4 is a schematic view of surfaces of a ball and cup joint prosthesis of the invention.

Referring now to FIG. 1, the ball 14 and cup 18 are shown in articulating contact with one another, and it will be understood that the differences in curvatures of the confronting surfaces of the ball and cup in this figure and also in FIG. 4 have been exaggerated for ease of understanding. The area of contact within the solid angle $\phi$ is referred to herein as the "area of intimate contact", and within this area, the surface of the cup is formed on radius $R_1$ and the surface of the ball is formed on radius $R_3$. Beyond the area of intimate contact, the surfaces of the ball and cup diverge. Immediately adjacent the area of intimate contact, the radius of the ball is indicated as $R_2$ and the radius of the cup as $R_4$.

Within the area of intimate contact, $R_1$ differs from $R_3$ by no more than 50 micrometers, desirably by no more than 25 micrometers, preferably by no more than 6 micrometers, and most preferably by no more than 2 micrometers. The area of contact subtended by the solid angle $\phi$ ranges from 0.12 $\pi R_3^2$ to 1.65 $\pi R_3^2$, and preferably from 0.2 $\pi R_3^2$ to 0.7 $\pi R_3^2$, as measured when the ball is gently received within the cup (that is, without significant compressive loading between the ball and cup). As discussed in greater detail below, the articulating surfaces of the ball and cup desirably have certain maximum surface roughnesses, and it will be understood that the radii $R_1$, $R_2$, $R_3$ and $R_4$ are measured to the surfaces of the ball and cup as defined by the tips of the surface asperities as measured by a standard coordinate measuring device such as a Sheffield-Bendix Formax model 6060 instrument using a 1.6 mm carbide ball as a probe tip. Such an area of intimate contact would not exist in a conventional metal-to-metal ball and cup prosthesis with the radius of curvature of the ball slightly smaller than that of the cup. As mentioned previously, with conventional metal-to-metal prostheses, high initial wear occurs, and a zone develops in which the surfaces fit with some snugness and have about the same radii of curvature, the zone being bounded by ridges. By providing an area of intimate contact as described herein, such initial wear largely can be avoided. With conventional metal-to-metal implants, most of the wear occurs in the first year or two following implantation. By largely avoiding this initial wear, we may reduce the total wear significantly over the life of the implant.

For ease of understanding, the area of intimate contact shown in FIG. 1 has its center at the apex A of the ball and cup. From FIG. 2, it will be understood that the actual compressive load axis between the ball and cup does not necessarily pass through the apexes of the ball and cup, but instead is inclined from the vertical (assuming a standing position) by an angle A ranging from about 15° to about 35°. It is important that the area of intimate contact as described and defined above be intersected by the load axis through all normal movements of the femur with respect to the pelvis. The area of intimate contact is shown in FIG. 1 as extending through the angle $\phi$ uniformly about the surface of the ball. Desirably, the angle $\phi$ is large enough to accommodate various alignments of the ball and cup and the position of the load axis so that the latter passes through the area of intimate contact. It may be desirable to shift the axis extending through the center of the area of intimate contact slightly away from the apex of the ball or cup or both so that the area of intimate contact is not symmetric about the apex of the ball or cup but rather is oriented to better contain the shifting load axis.

The articulating hard surfaces of the ball and socket each preferably are made from a hard metal such as cobalt-chrome alloys. Metals such as titanium and titanium alloys preferably are avoided because of their low galling resistance. Ceramic materials also may be used. References herein to "hard" surfaces should be understood to refer to surfaces having surface hardness values not less than about 170 Knoop. The articulating surfaces may be carefully shaped by known superfinishing grinding or lapping processes. Articulating metal surfaces may be hardened by known methods including ion bombardment and the like. Polishing of the resulting surfaces can be done in the usual fashion with a superfinishing machine using a very fine abrasive, care being taken to preserve the congruency of the articulating surfaces of the ball and cup. The shaped surfaces may also be coated with a hard coating such as a diamond-like coating or with a nitride such as titanium nitride. When the articulating surfaces are of metal, it is preferred to employ different metals, or different alloys of similar metals, for the respective surfaces, with the result that the levels of wear resistance of the two materials are different. For example, the surface of the ball may be of a low carbon cobalt-chrome alloy and the surface of the cup of a high carbon cobalt-chrome alloy.

Also important to the present invention is the nature of the confronting surfaces of the ball and cup in the area immediately adjacent the area of intimate contact. In this area, referred to herein as a "non contact" area, the radius on which the surface of the ball is formed is slightly less than that of the cup. It is desired that the surfaces of the cup and ball diverge from one another gradually in this non-contact area, and it is believed that the very gradual divergence of these surfaces contributes to the ease with which synovial fluid is received between the cup and ball surfaces in the area of intimate contact and to permit the avoidance of ridges which could contribute to increased wear.

FIG. 1 depicts the interior of the cup as being spherical and the ball being formed on the same radius as the cup at the center of the area of intimate contact and a smaller radius toward its equator, and this is the preferred embodiment. The ball may be made spherical instead, and its surface may be formed on the same radius as the cup at the center of the area of intimate contact and may be formed on a larger radius outside the area of intimate contact as the equator is approached. For that matter, outside the area of intimate contact, the radius of the ball may be decreased to a smaller value and the radius of the cup may be increase to a larger value as the equator is approached, so long as the relationship between the gap and the angle $\theta$ is substantially as described above. In the latter case, distance s would be located on the arc swept out by the radius $R_1$, and would lie between the confronting surfaces of the ball and cup. In any event, in order to better avoid the formation of ridges adjacent the area of intimate contact, the radii $R_2$ and $R_4$ each preferably has its origin along a line passing through both the origin of the radius $R_1$ and the edge of the area of intimate contact.

When, as in FIG. 1, the interior surface of the cup is spherical ($R_1=R_4$) and the surface of the ball outside the area of intimate contact is formed on a lesser radius, the gap "h" between confronting surfaces of the ball and cup at a distance s from the edge of the area of intimate contact measured along the arc swept out by the radius $R_1$; that is, along the curved surface of the cup away from its apex, is within 20% of the value given by the expression $s^2/2R$ in which the effective radius $R=(R_4R_2)/(R_4-R_2)$ where $R_2$ and $R_4$ are the radii of the ball and of the cup, respectively, immediately adjacent the area of intimate contact. Phrased another way, for a given position on the surface of the cup spaced from the area of intimate contact by the angle $\theta$ (as shown in FIG. 1 as the angle swept out by the radius $R_1$ away from the area of intimate contact, the gap h is within 20% of the value of the approximate expression $(R_1\theta)^2/2R$ in which R is as defined above. When $\theta$ is less than about 0.5 radians, the expression $(R_1\theta)^2/2R$ defines the gap h within plus or minus 3%.

Similarly, when the exterior surface of the ball is spherical ($R_2=R_3$) and the surface of the cup outside the area of intimate contact is formed on a larger radius, the gap h between confronting surfaces of the ball and cup at a distance s from the edge of the area of intimate contact measured along the arc swept out by the radius $R_3$, that is, along the curved surface of the ball away from its apex is within 20% of the value given by the expression $s^2/2R$ in which R is as given above. Phrased another way, for a given position on the surface of the cup spaced from the area of intimate contact by the angle $\theta$ (as shown in FIG. 1 as the angle swept out by the radius $R_3$ away from the area of intimate contact, the gap $h_2$ is within 20% of the value of the approximate expression $(R_3\theta)^2/2R$ in which R is as defined above and $\theta$ is expressed in radians. When $\theta$ is less than about 0.5 radians, the expression $(R_3\theta)^2/2R$ defines the gap h within plus or minus 3%.

Since, in the area of intimate contact, $R_1$ and $R_3$ are essentially equal, the expressions $(R_3\theta)^2/2R$ and $(R_1\theta)^2/2R$ are essentially equivalent and can be represented by the latter expression. Although this expression is not precise, it closely approximates the gap h measured along a line extending through the origin of $R_1$ and the confronting surfaces of the ball and cup, and is useful not only when $R_1=R_4$ or $R_2=R_3$, but also when neither of these expressions apply, that is, when the surfaces of the cup and ball outside the area of intimate contact are formed on radii different from the cup and ball radii within the area of intimate contact.

Thus, it should be understood that the confronting surfaces of the ball and cup diverge quite gradually away from the area of intimate contact, and ridges on the cup or ball are avoided. The nature of the surfaces in the area of intimate contact is such that the surfaces slide over one another with a small amount of wear distributed over the area of intimate contact. It is beneficial to have a large, well lubricated area of intimate contact. The rate at which the surfaces diverge outside of the area of intimate contact is a function of the effective radius R, as given above. R desirably is in the range of 1 to 14 meters, and preferably in the range of 3 to 10 meters.

FIG. 4 illustrates articulating surfaces of a cup and ball a cup and ball in the situation where the surfaces of the cup and ball outside the area of intimate contact are formed on radii different from the cup and ball radii within the area of intimate contact, positions on the cup and ball being located in an X-Y coordinate system having its origin at the center of the area of intimate contact with the X axis perpendicular to the contacting surfaces of the ball and cup at the center of the area on intimate contact. Here, the gap "g" is measured at any given value of X in the non contact area, that is, parallel to the Y axis, and is given by the expression $$g=(R_2-R_4)(1-D^2)^{1/2}+[R_4^2-(X^*-R_4D)^2]^{1/2}-[R_2^2-(X^*-R_2D)^2]^{1/2},$$

where $X^*=X-R_1(1-D)$ and $D=\cos(\phi/2)$.

Surface roughness of the articulating surfaces also has an influence on wear. The centerline average surface roughness of both the ball and cup articulating surfaces, as measured by a profile measuring machine such as a Sheffield profilometer, is not greater than 0.1 micrometers and preferably is not greater than 0.025 micrometers. With ceramic materials, a surface roughness of 0.0125 micrometers or less may be obtained and is preferred. As with any metal surface, the articulating surfaces of the ball and cup consist of a series of peaks and valleys when viewed at a microscopic level, and when microscopically rough surfaces rub against one another, some wear will occur as the peaks of the respective surfaces encounter one another. In accordance with the present invention, however, it is not enough that the respective articulating surfaces have smooth surfaces. It is also required that the area of intimate contact of these surfaces be in the range of 0.12 $\pi R_3^2$ to 1.65 $\pi R_3^2$. Desirably, the confronting surfaces of the cup and ball adjacent the area of intimate contact diverge in a ridge-free and gradual manner so as to promote lubricant entrainment.

As a result of the invention, the articulating hard surfaces of the ball and cup joint wear very little, thereby releasing little in the way of harmful debris into the joint space.

While a preferred embodiment of the present invention has been described, it should be understood that various changes, adaptations and modifications may be made therein without departing from the spirit of the invention and the scope of the appended claims.

What is claimed is:

1. An articulating joint prosthesis for use between two normally articulating bones, comprising
   an articulating cup member attachable to one of the bones and comprising a body having a generally hemispheric cavity provided with a spheroidal internal surface including a first hard spheroidal articulating surface formed on a radius $R_1$,
   an articulating ball member attachable to the other of said bones and having a generally ball-shaped body provided with a spheroidal surface including a second hard spheroidal articulating surface formed on a radius $R_3$ and slidingly contacting said first articulating surface in an area of intimate contact in which $R_1$ differs from $R_3$ by no more than 50 micrometers,
   the respective first and second articulating surfaces being configured so that the area of intimate contact ranges from 0.12 $\pi R_3^2$ to 1.65 $\pi R_3^2$.

2. The articulating joint prosthesis of claim 1 wherein said respective first and second spheroidal surfaces are configured so that the area of intimate contact ranges from 0.2 $\pi R_3^2$ to 0.7 $\pi R_3^2$.

3. The articulating joint prosthesis of claim 1 wherein said respective first and second spheroidal surfaces diverge immediately adjacent said area of intimate contact to provide a closely spaced but non contact area between said spheroidal surfaces, the configuration of said surfaces in the non contact area being characterized by the relationship $h=(R_1\Theta)^2/2$ R±20% in which h is the gap between said diverging surfaces at a location spaced away from the area of intimate contact by the angle $\Theta$ swept out by the radius $R_3$, and $R=(R_4R_2)/(R_4-R_2)$ where $R_2$ and $R_4$ are the radii of the spheroidal surfaces of the ball and cup, respectively, immediately adjacent the area of intimate contact.

4. The prosthesis of claim 3 wherein $R_2$ is smaller than $R_3$.

5. The prosthesis of claim 3 wherein $R_4$ is greater than $R_1$.

6. The prosthesis of claim 3 wherein $R_1=R_4$.

7. The prosthesis of claim 3 wherein $R_2=R_3$.

8. The prosthesis of claim 3 wherein R, in meters, ranges from 1 to 14.

9. The prosthesis of claim 3 wherein the configuration of said surfaces in the non contact area at a location spaced away from the area of intimate contact by said angle $\Theta$ where $\Theta$ is less than 0.5 radians is characterized by the relationship $h=(R_1\Theta)^2/2$ R±3%.

10. The prosthesis of claim 3 or claim 9 wherein said surfaces in the non contact area at a position X are characterized by the relationship $$g=(R_2-R_4)(1-D^2)^{1/2}+[R_4^2-(X^*-R_4D)^2]^{1/2}-[R_2^2-(X^*-R_2D)^2]^{1/2},$$

where $X^*=X-R_1(1-D)$, $D=\cos(\phi/2)$, and $R=(R_4R_2)/(R_4-R_2)$, and wherein X, Y is located on an X-Y coordinate system having its origin at the center of the area of intimate contact with the X axis perpendicular to the contacting surfaces of the ball and cup at the center of the area on intimate contact, and where g is the gap between said spheroidal surfaces in the non contact area measured parallel to the Y axis at said position X.

11. The prosthesis of claim 1 wherein the first and second articulating surfaces in the area of intimate contact are each characterized by a centerline average surface roughness of not greater than 0.1 micrometers.

12. The prosthesis of claim 1 wherein the first and second articulating surfaces in the area of intimate contact are each characterized by a centerline average surface roughness of not greater than 0.025 micrometers.

13. An articulating joint prosthesis for use between two normally articulating bones, comprising
   an articulating cup member attachable to one of the bones and comprising a body having a generally hemispheric cavity provided with a spheroidal internal surface including a first hard spheroidal articulating surface formed on a radius $R_1$,
   an articulating ball member attachable to the other of said bones and having a generally ball-shaped body provided with a spheroidal surface including a second hard spheroidal articulating surface formed on a radius $R_3$ and slidingly contacting said first articulating surface in an area of intimate contact in which $R_1$ differs from $R_3$ by no more than 50 micrometers, said ball and cup having gradually diverging surfaces outside the area of intimate contact formed respectively on radii $R_2$ and $R_4$,
   the respective first and second articulating surfaces in the area of intimate contact being configured so that the area of intimate contact ranges from 0.12 $\pi R_3^2$ to 1.65 $\pi R_3^2$, said respective first and second spheroidal surfaces diverging gradually immediately adjacent said area of intimate contact to provide a non contact area between said spheroidal surfaces characterized by the relationship at a position X $$g=(R_2-R_4)(1-D^2)^{1/2}+[R_4^2-(X^*-R_4D)^2]^{1/2}-[R_2^2-(X^*-R_2D)^2]^{1/2},$$

where $X^*=X-R_1(1-D)$, $D=\cos(\phi/2)$, and $R=(R_4R_2)/(R_4-R_2)$, and wherein X is located on an X-Y coordinate system having its origin at the center of the area of intimate contact with the X axis perpendicular to the contacting surfaces of the ball and cup at the center of the area on intimate contact, and where g is the gap between said spheroidal surfaces in the non contact area measured parallel to the Y axis at said position X, wherein R, in meters, ranges from 1 to 14, and wherein the first and second articulating surfaces in the area of intimate contact are each characterized by a centerline average surface roughness of not greater than 0.1 micrometers.

14. The prosthesis of claim 13 wherein said respective first and second spheroidal surfaces are configured so that the area of intimate contact ranges from 0.2 $\pi R_3^2$ to 0.7 $\pi R_3^2$.

15. The prosthesis of claim 13 wherein $R_2$ is smaller than $R_3$.

16. The prosthesis of claim 13 wherein $R_4$ is greater than $R_1$.

17. The prosthesis of claim 13 wherein $R_1=R_4$.

18. The prosthesis of claim 13 wherein $R_2=R_3$.

19. The prosthesis of claim 13 wherein the first and second articulating surfaces in the area of intimate contact are each characterized by a centerline average surface roughness of not greater than 0.025 micrometers.

20. The prosthesis of claim 13 wherein one of the articulating surfaces of the ball or cup is formed on a constant radius both within and outside the area of intimate contact and the other surface is not.

* * * * *